(12) United States Patent
Wang et al.

(10) Patent No.: US 12,403,330 B1
(45) Date of Patent: Sep. 2, 2025

(54) BORON NEUTRON CAPTURE THERAPY SYSTEM

(71) Applicant: Huapeng Neutron Technology (Hangzhou) Co., Ltd., Hangzhou (CN)

(72) Inventors: Sheng Wang, Hangzhou (CN); Yaocheng Hu, Hangzhou (CN); Jingjing Fan, Hangzhou (CN); Yupeng Xie, Hangzhou (CN); Dongxu Yang, Hangzhou (CN)

(73) Assignee: HUAPENG NEUTRON TECHNOLOGY (HANGZHOU) CO., LTD., Hangzhou (CN)

( * ) Notice: Subject to any disclaimer, the term of this patent is extended or adjusted under 35 U.S.C. 154(b) by 0 days.

(21) Appl. No.: 19/212,751

(22) Filed: May 20, 2025

(30) Foreign Application Priority Data

Jun. 25, 2024 (CN) .......................... 202410822930.9

(51) Int. Cl.
 *A61N 5/10* (2006.01)
 *G21G 4/02* (2006.01)
 *H05H 3/06* (2006.01)

(52) U.S. Cl.
 CPC .......... *A61N 5/1077* (2013.01); *A61N 5/1048* (2013.01); *G21G 4/02* (2013.01); *H05H 3/06* (2013.01); *A61N 2005/1074* (2013.01); *A61N 2005/109* (2013.01)

(58) Field of Classification Search
 CPC ............... A61N 5/1077; A61N 5/1048; A61N 2005/1074; A61N 2005/109; G21G 4/02; H05H 3/06
 See application file for complete search history.

(56) References Cited

U.S. PATENT DOCUMENTS 9,636,524 B2 * 5/2017 Pantell ..................... G21G 4/02
11,400,316 B2 * 8/2022 Liu ........................... A61N 5/10
(Continued)

FOREIGN PATENT DOCUMENTS

| CN | 104934803 A | 9/2015 |
| CN | 109011206 A | 12/2018 |
| CN | 114550960 A | 5/2022 |

*Primary Examiner* — David A Vanore
(74) *Attorney, Agent, or Firm* — Bayramoglu Law Offices LLC

(57) ABSTRACT

A boron neutron capture therapy system includes a beam shaping body with a proton channel and a replaceable target assembly slidably disposed inside the proton channel, where a current monitoring apparatus is disposed outside the beam shaping body, the target assembly is provided with a moving contact, and the current monitoring apparatus is provided with a stationary contact forming a moving contact conductive mode with the moving contact. For the boron neutron capture therapy system, the current monitoring apparatus and the target assembly are connected through a moving contact conductive mode, avoiding the influence on the movement, automatic replacement, storage and the like of the target assembly caused by hard-wired connection, operations such as automatic adjustment, contact for power-on and non-contact for power-off can be performed, a target current can be measured and read in real time under full automation, the manual disconnection operation is not needed.

20 Claims, 12 Drawing Sheets

(56) References Cited

U.S. PATENT DOCUMENTS

| | | | | |
|---|---|---|---|---|
| 11,740,370 B2* | 8/2023 | Liu | ............ | H05H 3/06 |
| | | | | 250/391 |
| 2018/0001112 A1* | 1/2018 | Liu | ............ | G21G 4/02 |
| 2018/0169440 A1* | 6/2018 | Liu | ............ | A61N 5/1075 |
| 2018/0326225 A1* | 11/2018 | Liu | ............ | G21G 4/02 |
| 2021/0060360 A1* | 3/2021 | Liu | ............ | G21K 1/00 |
| 2022/0100985 A1* | 3/2022 | Wang | ............ | G06F 18/10 |

* cited by examiner

BORON NEUTRON CAPTURE THERAPY SYSTEM

CROSS REFERENCE TO THE RELATED APPLICATIONS

This application is based upon and claims priority to Chinese Patent Application No. 202410822930.9, filed on Jun. 25, 2024, the entire contents of which are incorporated herein by reference.

TECHNICAL FIELD

The present invention relates to the technical field of boron neutron capture therapy, and particularly to a boron neutron capture therapy system.

BACKGROUND

Target current monitoring is a common requirement for target state and accelerator state measurement. Since the beam accelerated by an accelerator includes charged particles, it will be conducted as a current after being deposited on a target.

In order to extract the current of the target, the target needs to be insulated from multiple components such as an accelerator and a beam shaping body, and then the insulated target is connected with an ammeter through an electric wire for reading.

For boron neutron capture therapy, the position of a fixed target is different from that in other neutron source application scenarios. The target is surrounded by a beam shaping system, and the target has a relatively high radioactivity. If the target is directly connected with an ammeter by an electric wire, when replacing the target, the electric wire will pull the ammeter and affect the apparatus. At the same time, there is a need to manually release the connection between the target and the ammeter in a radiation environment, which poses a radiation problem. In addition, if the electric wire is too long, it is not convenient to store the target in a waste target box. If the electric wire is pinched at the opening and closing part of the waste target box, radioactive leakage will occur.

Therefore, there is an urgent need to design a device for monitoring the dark current of the target in a comprehensive environment such as boron neutron capture therapy, automatic target replacement and replacement of a moderator to adjust the beam. The device can read the target current under full automation without affecting the automatic replacement and storage of the target, and without restricting the adjustment of the position of the target in the beam shaping body BSA when replacing the moderator.

SUMMARY

The objective of the present invention is to solve the problems existing in the current monitoring of the dark current of the target in a comprehensive environment such as boron neutron capture therapy, target replacement and replacement of the moderator to adjust the beam, including that the electric wire will pull the ammeter and affect the apparatus, there is a radiation impact when manually disconnecting the connection between the target and the ammeter in a radiation environment, and in addition, there will be radioactive leakage during the process of storing the waste target due to the long electric wire. The present invention provides a boron neutron capture therapy system that can read the current of the target under full automation without affecting the automatic replacement and storage of the target, and without restricting the adjustment of the position of the target in the beam shaping body BSA when replacing the moderator.

The technical solution adopted by the present invention to achieve its inventive objective is as follows: a boron neutron capture therapy system, including a beam shaping body with a proton channel and a replaceable target assembly disposed inside the proton channel, where a current monitoring apparatus is disposed outside the beam shaping body, the target assembly is provided with a moving contact, and the current monitoring apparatus is provided with a stationary contact forming a moving contact conductive mode with the moving contact. For the boron neutron capture therapy system, a current monitoring apparatus for real-time target current monitoring is disposed outside the beam shaping body. In view of the characteristics that the target assembly needs to be replaced and slide inside and outside the proton channel according to the usage situation, direct hard connection by a conductive wire is not adopted between the current monitoring apparatus and the target assembly, but the current monitoring apparatus and the target assembly are connected through a moving contact conduction mode. This avoids the influence on the automatic replacement and storage of the target assembly, and also does not impose restrictions on the adjustment of the position movement of the target assembly inside the beam shaping body when replacing the moderator. It enables the operations of automatic adjustment, contact for power-on and contact disconnecting for power-off. In order to achieve the moving contact conduction mode, a moving contact is disposed on the target assembly and a stationary contact is disposed on a current monitoring apparatus. The moving contact moves together with the target assembly, while the stationary contact can be disposed relatively statically on the current monitoring apparatus. As long as the current monitoring apparatus is not moved and is disposed outside the beam shaping body where it can be in contact with the moving contact, the contact circuit conduction between the target assembly and the current monitoring apparatus can be achieved. When the contact is released, an open circuit is formed, achieving fully automatic monitoring of the dark current of the target without the need for manual operation to release the connection between the target assembly and the current monitoring apparatus. The boron neutron capture therapy system is used for measuring the dark current of the target in a comprehensive environment such as boron neutron capture therapy, automatic target replacement and replacement of the moderator to adjust the beam, and can measure and read the current of the target in real time under full automation. It solves the problems that in the automatic target replacement and target storage processes, there is a need to manually release the connection between the target and the current monitoring apparatus in a radiation environment, which not only poses a radiation risk but also is not conducive to automated operation. Fully automatic and rapid target replacement is achieved through automatic devices such as manipulators, the position of the target assembly is quickly moved and adjusted arbitrarily as required to meet the needs of the target assembly extending into different positions inside the beam shaping body, and rapid and automatic storage of the waste target can be achieved.

Preferably, the moving contact and the stationary contact are disposed on a contact circuit device implementing the moving contact conductive mode. In order to achieve the connection in the moving contact conduction mode, a contact circuit device is disposed between the target assembly and the current monitoring apparatus. The moving contact and the stationary contact are disposed on the contact circuit device. Through the contact circuit device, a contact conduction circuit can be achieved as required, and an open circuit is formed when there is no contact, effectively avoiding the influence such as pulling on the current monitoring apparatus during the movement and replacement of the target assembly.

Preferably, the contact circuit device includes an adjustable positioning on-off assembly slidably disposed on the target assembly and a contact conductive assembly disposed outside the beam shaping body. The contact circuit device is mainly achieved through the adjustable positioning on-off assembly disposed on the target assembly and the contact conductive assembly disposed outside the beam shaping body. The adjustable positioning on-off assembly can slide axially along the target assembly and is configured to adjust the position of the target assembly extending into the beam shaping body. No matter how the position of the target assembly extending into the beam shaping body changes, the adjustable positioning on-off assembly can be in contact with the external contact conductive assembly for conduction, and perform the operation of powering off when there is no contact. Moreover, this contact circuit is respectively disposed on the target assembly and outside the beam shaping body. In the replacement process of the target assembly, the adjustable positioning on-off assembly moves, is replaced and stored together with the target assembly, and does not interfere with the contact conductive assembly. There is no need for manual disconnection operation, which reduces the radiation risk and improves the operation efficiency of automatic target replacement.

Preferably, the moving contact is disposed on the adjustable positioning on-off assembly, and the stationary contact is disposed on the contact conductive assembly. When the adjustable positioning on-off assembly is in contact with the contact conductive assembly for conduction, a current monitoring circuit is formed among the target assembly, the adjustable positioning on-off assembly, the contact conductive assembly and the current monitoring apparatus. Through the contact between the adjustable positioning on-off assembly and the contact conductive assembly, a current monitoring circuit is formed among the target assembly, the adjustable positioning on-off assembly, the contact conductive assembly and the current monitoring apparatus, which can monitor the current in real time. When the contact is disconnected, there is no connection relationship among the components, and automatic operations such as the movement, replacement and storage of the target assembly can be achieved.

Preferably, the adjustable positioning on-off assembly includes an insulating sliding positioning part, a moving contact part is fixedly connected with the sliding positioning part, and the moving contact part is electrically connected to the target assembly through a conductive circuit. The adjustable positioning on-off assembly mainly uses a sliding positioning part insulated from the target assembly, and a moving contact part is fixed on the sliding positioning part. The conductive contact part is electrically connected to the target body in the target assembly through a relatively short or telescopic conductive circuit. When there is a need to extract and monitor the target current, as long as the moving contact part is in contact with the external contact conductive assembly, a circuit can be formed for detection.

Preferably, the moving contact is disposed on the moving contact part, or the moving contact part forms the moving contact. The moving contact can be a metal contact disposed on the moving contact part, or one of various shapes such as a metal spring contact and a metal probe; and the conductive moving contact part can also be directly set as the moving contact.

Preferably, the target assembly is provided with a sliding groove, and the sliding positioning part is slidably disposed inside the sliding groove and is located outside the beam shaping body. In order to adjust the position of the sliding positioning part relative to the target assembly and keep it outside the beam shaping body all the time, as a preferred solution, a sliding groove is disposed on the target assembly, and the axial sliding adjustment is achieved by the cooperation between the sliding positioning part and the sliding groove. The sliding groove can be directly formed on the target assembly, or can be achieved by fixing a sliding seat with the sliding groove on the target assembly. The position and shape of the sliding groove are not limited, as long as relative sliding can be achieved.

Preferably, the contact conductive assembly includes a stationary contact part disposed outside the beam shaping body and located at an outer edge of the proton channel, and the stationary contact part is electrically connected to the current monitoring apparatus. The contact conductive assembly is mainly achieved through a stationary contact part. The stationary contact part is electrically connected to the external current monitoring apparatus. Neither the stationary contact part nor the current monitoring apparatus needs to be manually disconnected or removed, and the automatic electrical connection between the target assembly and the current monitoring apparatus can be achieved.

Preferably, the stationary contact is disposed on the stationary contact part, or the stationary contact part forms the stationary contact. The stationary contact can be a metal contact disposed on the stationary contact part, or a metal spring contact, a metal sheet, etc., and can also be made of other conductive materials; and the conductive stationary contact part can also be directly set as the stationary contact.

Preferably, the stationary contact part is fixed outside the beam shaping body, or the stationary contact part is movably disposed on the beam shaping body. The stationary contact part can be directly fixed on a front reflector of the beam shaping body and near the outer edge of the proton channel. Alternatively, according to the need, a slideway can be disposed on the beam shaping body, and the contact conductive assembly is slidably disposed on the slideway to adjust the position of the contact conductive assembly, so as to meet the needs of the sliding positioning part on the target assembly being in different positions after being inserted into the proton channel. The purpose of the sliding of the contact conductive assembly is that when the target assembly is replaced, there is no need to consider the specific direction of the sliding positioning part.

Preferably, the target assembly includes a cylinder body and a target body, the target body is disposed at one end of the cylinder body extending into an interior of the beam shaping body, and the target body, the contact circuit device and the current monitoring apparatus form a circuit.

Preferably, the current monitoring apparatus includes an external monitoring and display device. By using an external monitoring and display device, the monitoring and display device can be disposed outside the beam shaping body, or can be disposed far away from the beam shaping body, that is, far away from the radiation source, which is convenient for real-time observation of the monitoring data in a radiation-free environment.

Preferably, a scale for implementing position adjustment is disposed on the target assembly. Disposing a scale on the target assembly facilitates adjustment of automatic target replacement and target position movement. It enables the adjustment of the distance that the target body extends into the beam shaping body according to the demand, making the adjustment more precise.

The beneficial effects of the present invention are as follows. (1) For the boron neutron capture therapy system, the current monitoring apparatus and the target assembly are connected through the moving contact conductive mode, avoiding the influence on the movement, automatic replacement, storage and the like of the target assembly caused by hard-wired connection, operations of automatic adjustment, contact for power-on and non-contact for power-off can be performed.

(2) The boron neutron capture therapy system is used for measuring the dark current of the target in a comprehensive environment such as boron neutron capture therapy, automatic target replacement and replacement of the moderator to adjust the beam, and can measure and read the current of the target in real time under full automation, meeting the needs of movement adjustment of the target extending into different positions inside the beam shaping body.

(3) The adjustable positioning on-off assembly moves, is replaced and stored together with the target assembly, and does not interfere with the contact conductive assembly. There is no need for manual disconnection operation, which reduces the radiation risk and improves the operation efficiency of automatic target replacement, movement, storage and monitoring.

In the figures: 1. beam shaping body; 2. target assembly; 21. moving contact; 3. current monitoring apparatus; 31. stationary contact; 4. proton channel; 5. contact circuit device; 6. cylinder body; 62. target vacuum tube section; 7. target body; 8. monitoring and display device; 9. connecting conductive wire; 10. adjustable positioning on-off assembly; 101. sliding positioning part; 102. moving contact part; 103. conductive circuit; 104. sliding body; 105. contact body; 11. contact conductive assembly; 111. insulating gasket; 112. stationary contact part; 12. sliding groove; and 13. sliding seat.

DETAILED DESCRIPTION OF THE EMBODIMENTS

The various aspects of the present invention will be described in detail below through specific embodiments in conjunction with the drawings.

Embodiment 1

Figure 1:
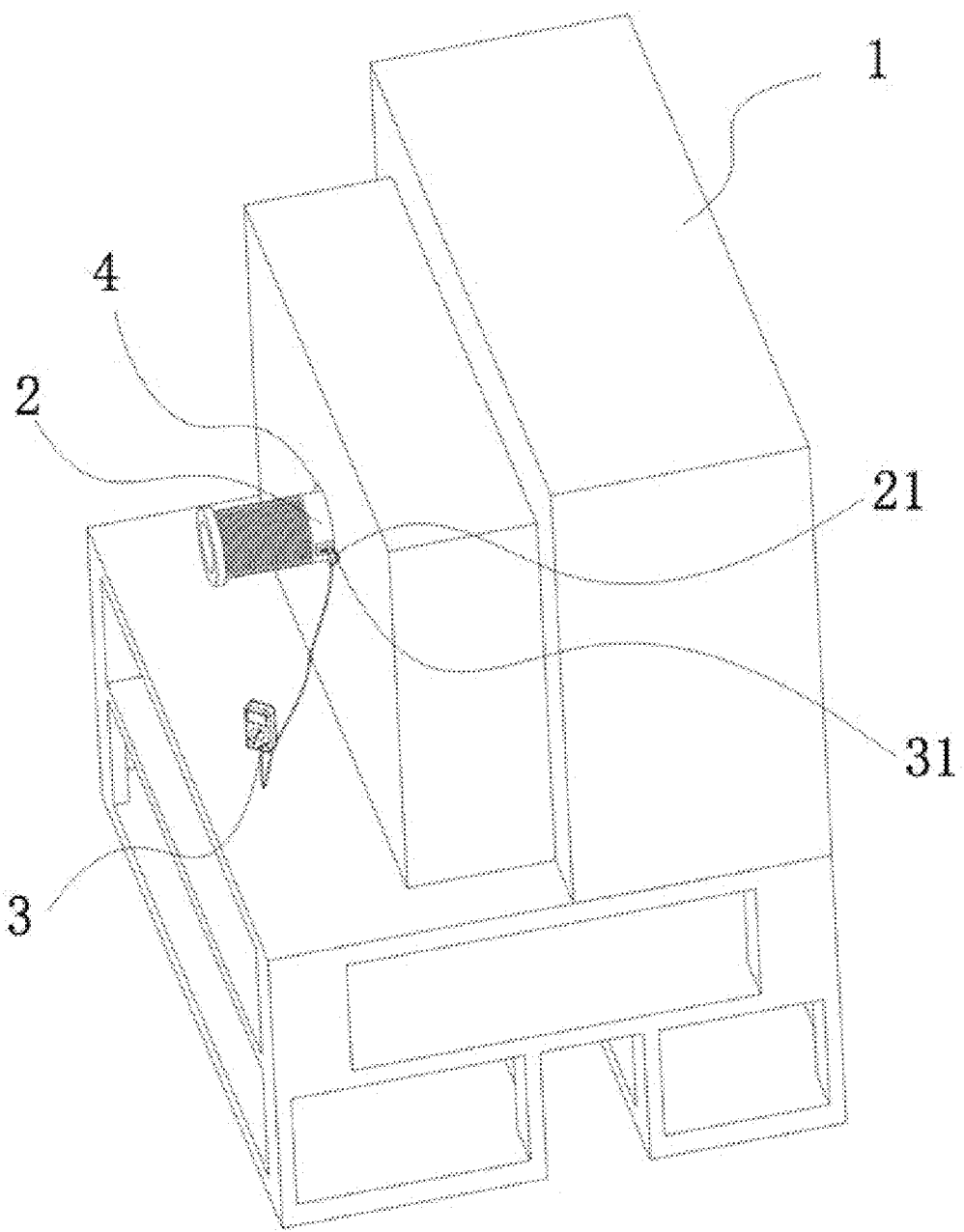
FIG. 1 is a schematic structural diagram of a boron neutron capture therapy system in the present invention.
Figure 5:
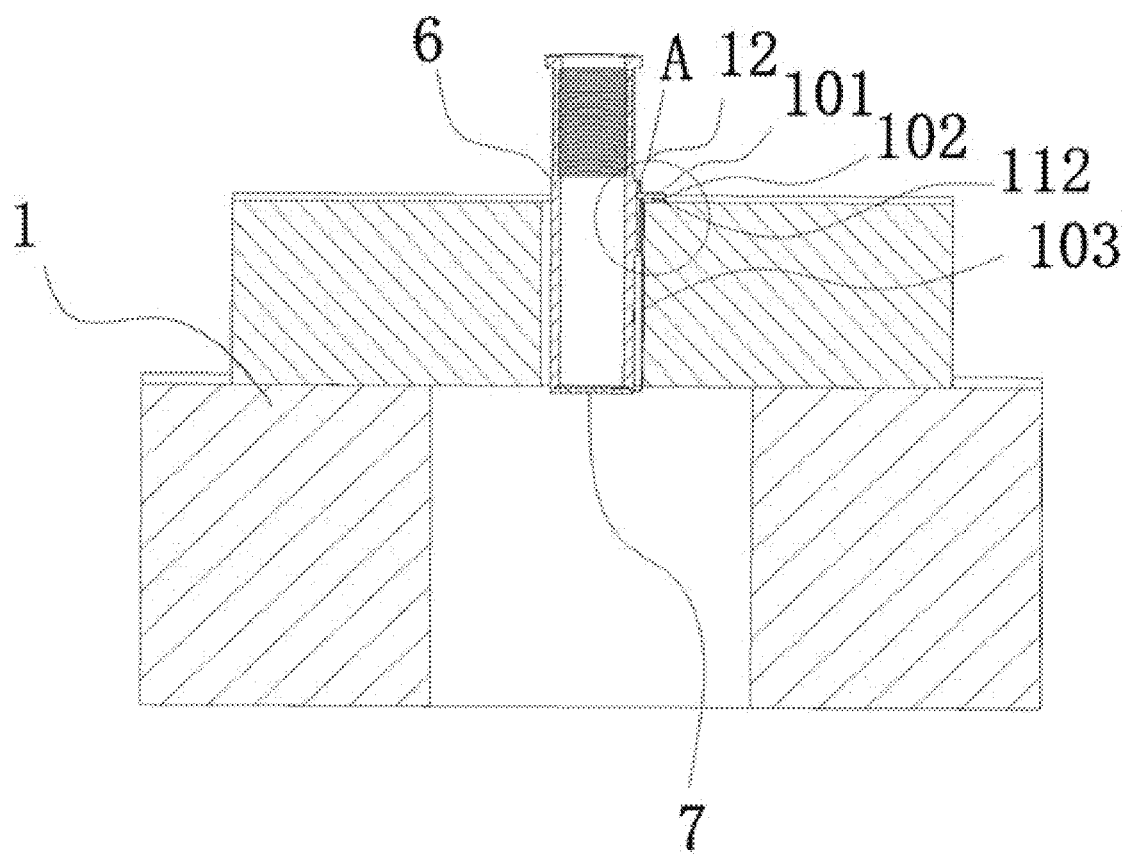
FIG. 5 is a cross-sectional view of a boron neutron capture therapy system in the present invention in another direction.

In the embodiments shown in FIG. 1 and FIG. 5, a boron neutron capture therapy system, including a beam shaping body 1 with a proton channel 4 and a replaceable target assembly 2 slidably disposed inside the proton channel 4 and can be replaced as required, where a current monitoring apparatus 3 is disposed outside the beam shaping body 1 near an outer edge of the proton channel 4, the target assembly 2 and the current monitoring apparatus 3 are connected in a moving contact conduction mode through a contact circuit device 5, instead of using hard-wired connection.

Figure 7:
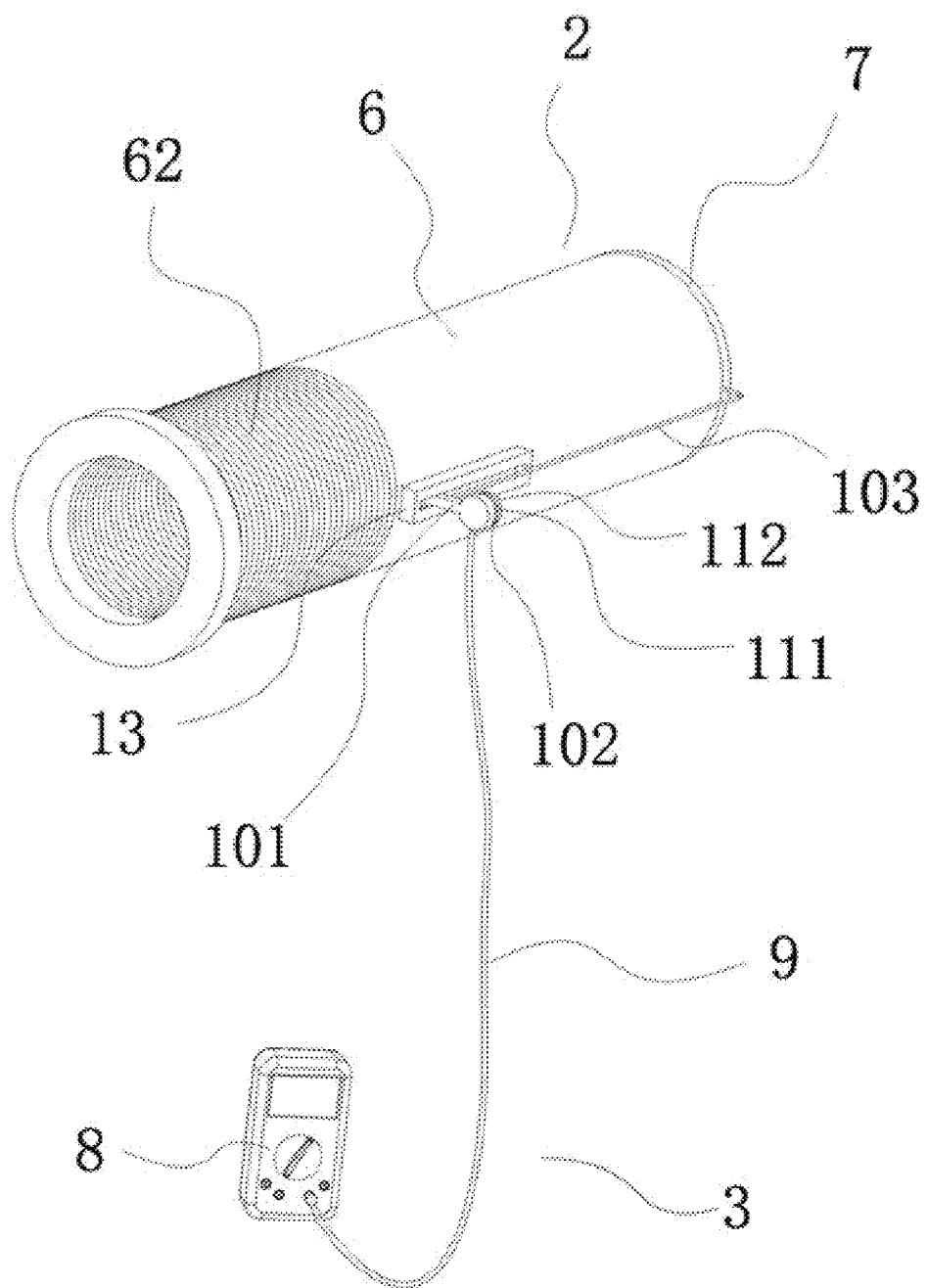
FIG. 7 is a schematic diagram of a connection structure between a contact circuit device and a target assembly in the present invention.
Figure 8:
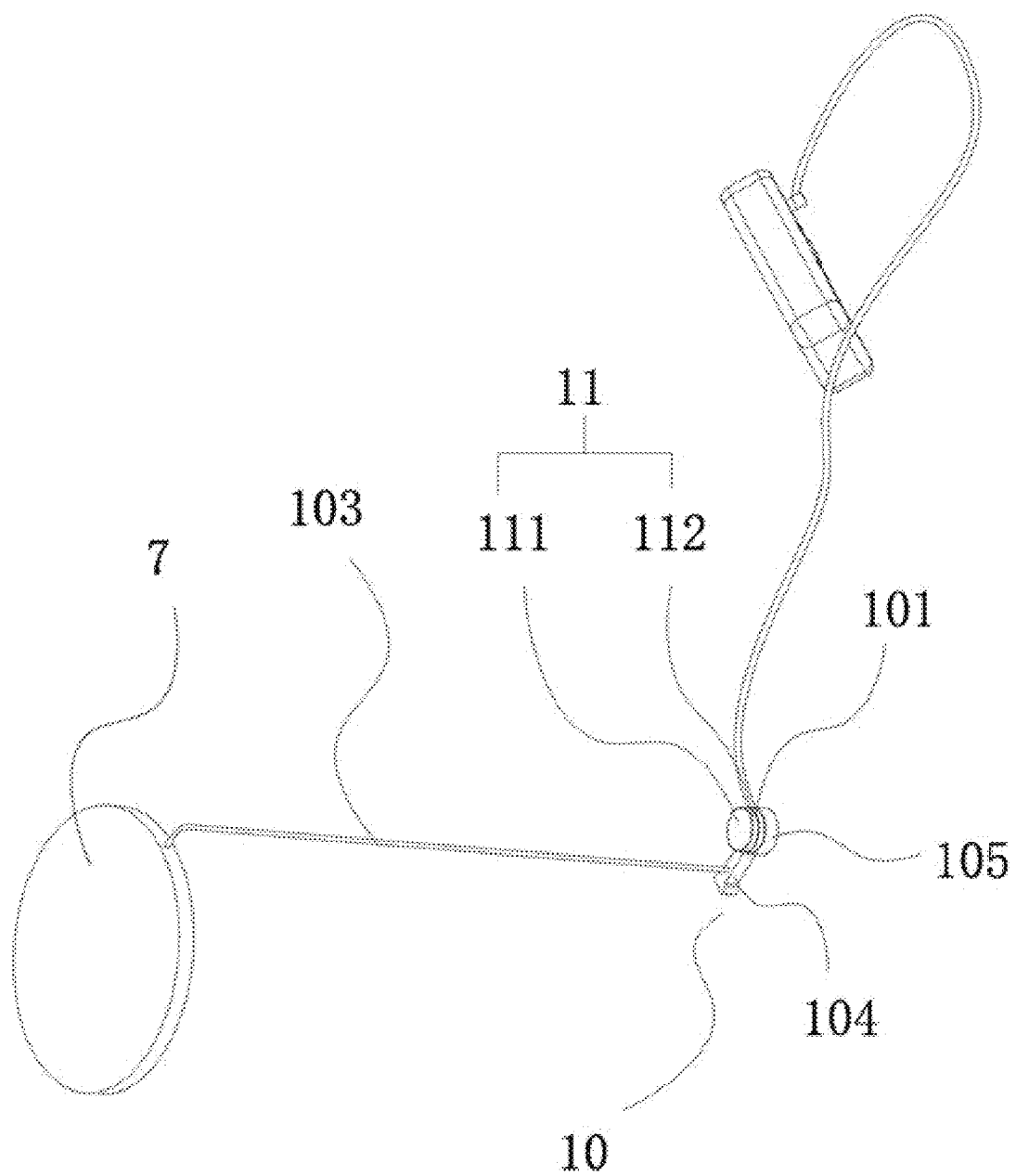
FIG. 8 is a schematic structural diagram of a contact circuit device in the present invention.

As shown in FIG. 7 and FIG. 8, the target assembly 2 includes a cylinder body 6 and a target body 7, the target body 7 is disposed at one end of the cylinder body 6 extending into an interior of the beam shaping body 1, and the target body 7, the contact circuit device 5 and the current monitoring apparatus 3 form a circuit.

In order to achieve connection in a moving contact conduction mode, the contact circuit device 5 includes an adjustable positioning on-off assembly 10 slidably disposed on the cylinder body 6 of the target assembly 2, and a contact conductive assembly 11 disposed outside the beam shaping body 1 and separably disposed from the adjustable positioning on-off assembly 10. When the adjustable positioning on-off assembly 10 is in contact with the contact conductive assembly 11 for conduction, a current monitoring circuit is formed among the target assembly 2, the adjustable positioning on-off assembly 10, the contact conductive assembly 11 and the current monitoring apparatus 3. When the adjustable positioning on-off assembly 10 is not in contact with the contact conductive assembly 11, an open circuit is formed among the target assembly 2, the adjustable positioning on-off assembly 10, the contact conductive assembly 11 and the current monitoring apparatus 3, and there is no conduction among them.

In order to achieve contact for a circuit and conduction and non-contact for an open circuit, the adjustable positioning on-off assembly 10 of the target assembly is provided with a moving contact 21, and the contact conductive assembly 11 of the current monitoring apparatus 3 is provided with a stationary contact 31 forming a moving contact conduction mode with the moving contact 21. The moving contact 21 and the stationary contact 31 achieve contact for a circuit and conduction and non-contact for an open circuit.

Figure 6:
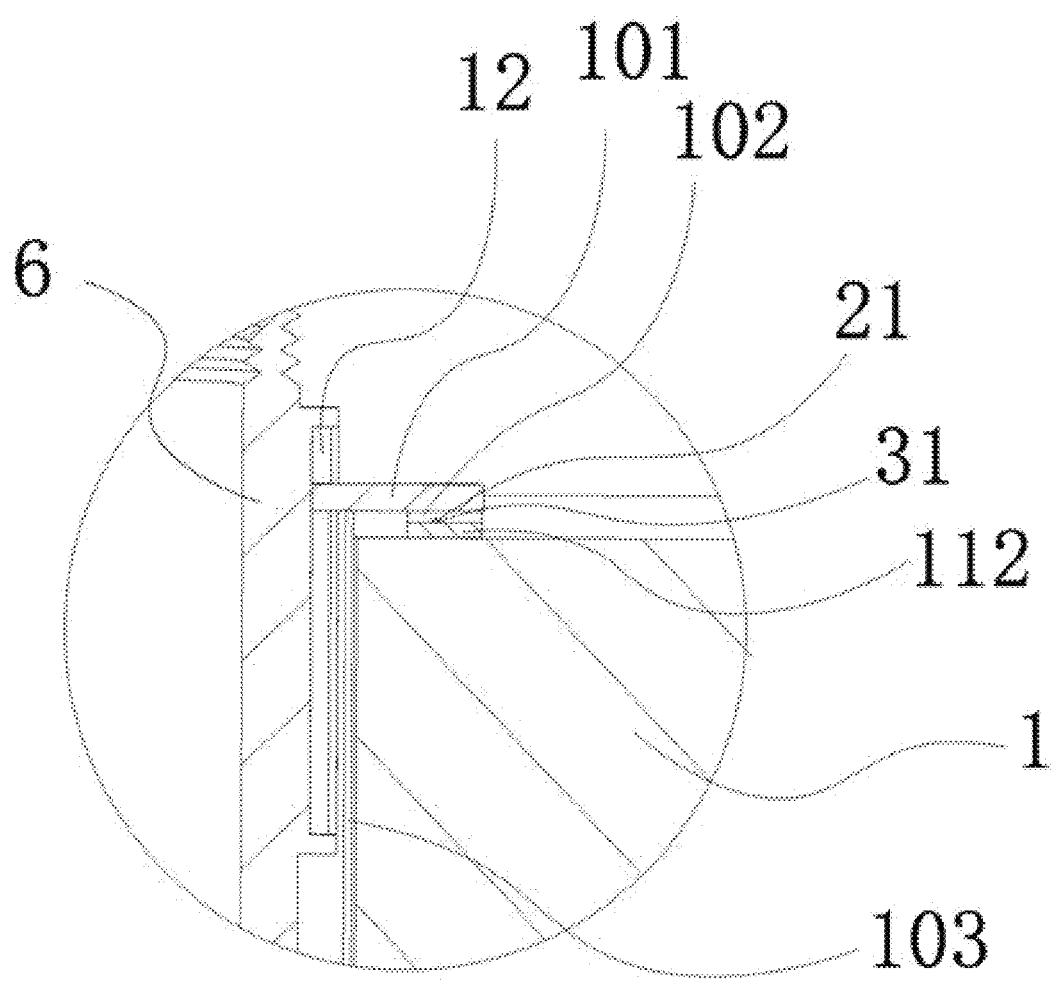
FIG. 6 is an enlarged view of part A in FIG. 5.
Figure 9:
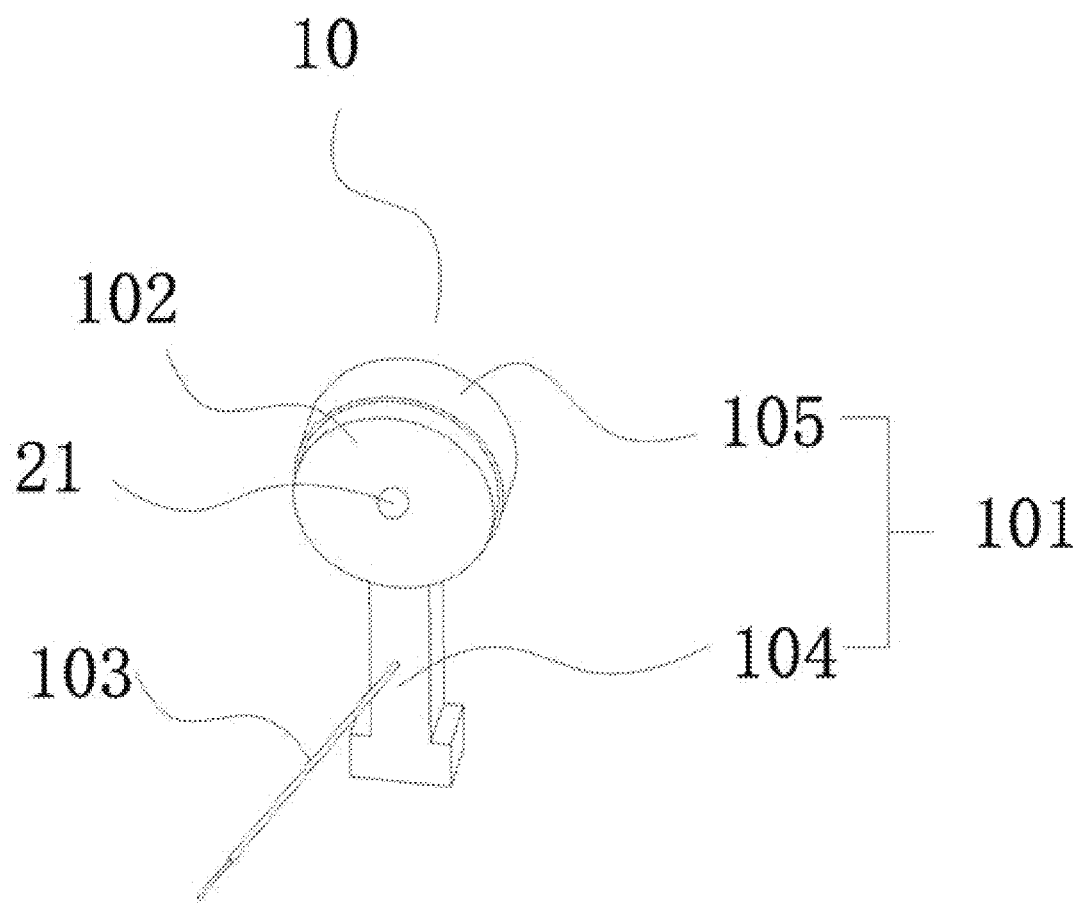
FIG. 9 is a schematic structural diagram of an adjustable positioning on-off assembly in the present invention.

As shown in FIG. 6 and FIG. 9, the adjustable positioning on-off assembly 10 mainly includes a sliding positioning part 101 insulated from the target assembly. A moving contact part 102 is fixedly connected with the sliding positioning part 101, and the moving contact part 102 is connected to the target body 7 through a conductive circuit 103; and the moving contact 21 is disposed on the moving contact part 102. In another embodiment, the moving contact part 102 forms the moving contact.

In order to enable axial sliding of the sliding positioning part 101 relative to the target assembly, target assembly 2 is provided with a sliding groove 12. The sliding positioning part 101 is slidably disposed inside the sliding groove 12. After the target assembly is mounted inside the proton channel, the sliding positioning part 101 is always outside the beam shaping body 1 and is limited by the outer edge of the proton channel 4.

The contact conductive assembly 11 includes a stationary contact part 112 disposed outside the beam shaping body 1 and located at the outer edge of the proton channel. The stationary contact part 112 is electrically connected to the current monitoring apparatus 3; and the stationary contact part 112 forms the stationary contact 31. In another embodiment, the stationary contact 31 is disposed on the stationary contact part 112.

The stationary contact part 112 is fixed outside the beam shaping body 1 near the outer edge of the proton channel 4, which is convenient for forming contact with the moving contact part 102 for conduction. In another embodiment, the stationary contact part 112 can also be movably disposed on the beam shaping body 1 in a way that it can move along the outer edge of the proton channel.

The current monitoring apparatus 3 includes a monitoring and display device 8 externally placed near or far away from the beam shaping body 1. The monitoring and display device 8 can be a milliammeter, an oscilloscope or any other apparatus that achieves a function of current monitoring and display.

Embodiment 2

Figure 2:
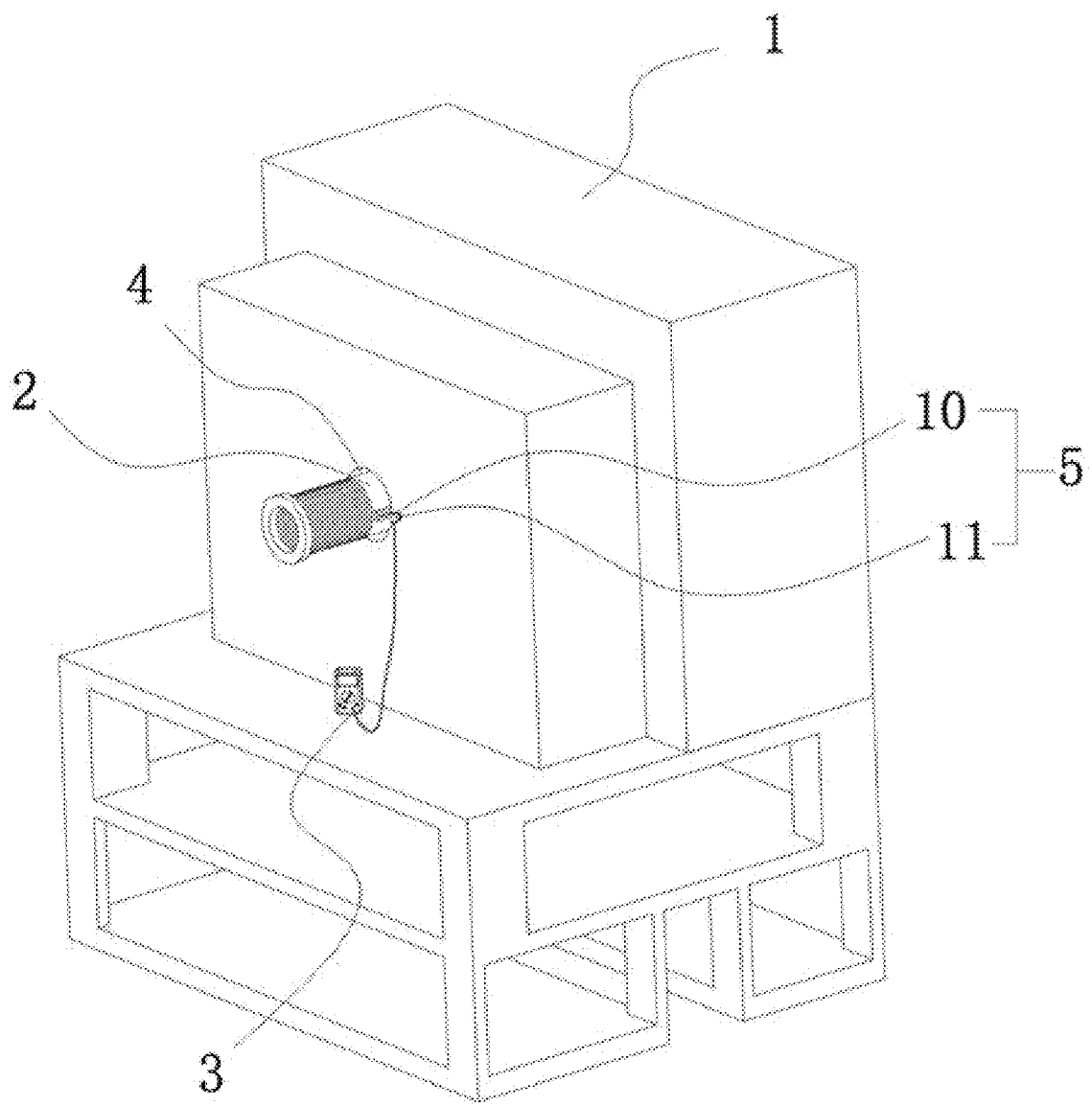
FIG. 2 is a schematic structural diagram of a boron neutron capture therapy system in the present invention from another angle.
Figure 3:
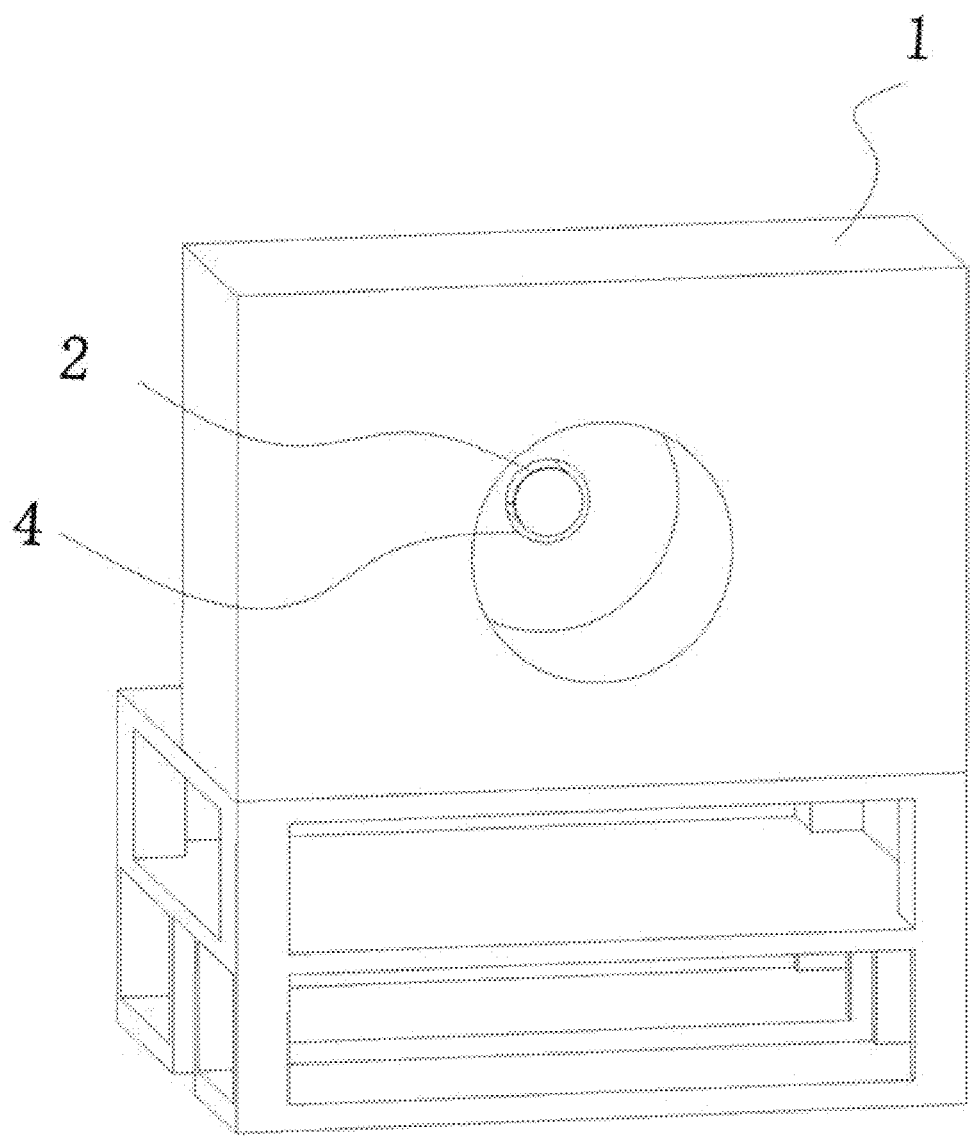
FIG. 3 is a schematic structural diagram of a boron neutron capture therapy system in the present invention from a rear view angle.
Figure 4:
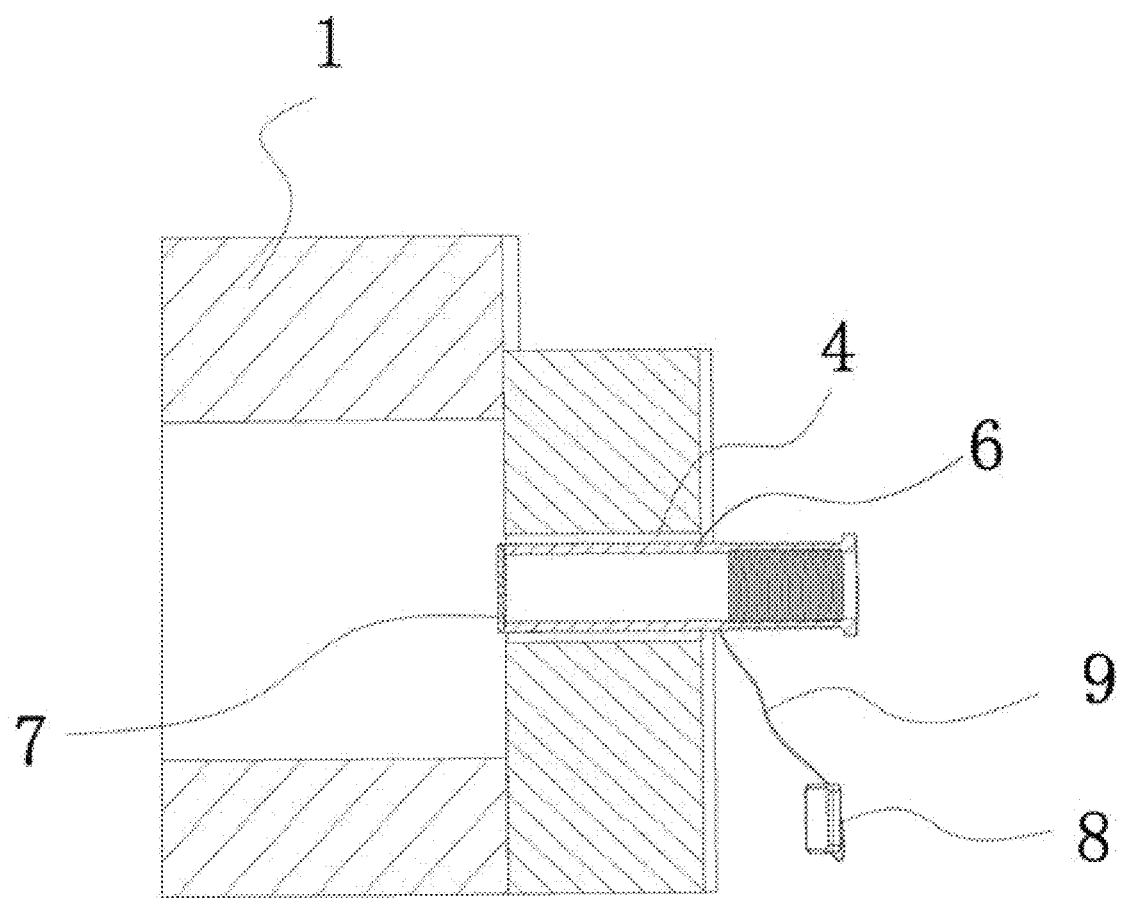
FIG. 4 is a cross-sectional view of a boron neutron capture therapy system in the present invention.

In the embodiments shown in FIG. 2, FIG. 3 and FIG. 4, a boron neutron capture therapy system, including a beam shaping body 1, a target assembly 2 and a current monitoring apparatus 3.

The beam shaping body 1 is provided with a proton channel 4 of the beam shaping body BSA cooperating with the target assembly 2.

The target assembly 2 is connected with the current monitoring apparatus 3 in a moving contact conduction mode, instead of directly using an electric wire connection conduction mode. In order to achieve connection in the moving contact conduction mode, a contact circuit device 5 is disposed between the target assembly 2 and the current monitoring apparatus 3.

The target assembly 2 includes a cylinder body 6 and a target body 7. The cylinder body 6 is connected with the target vacuum tube section 62. The target vacuum tube section 62 is an insulator. During use, the target vacuum tube section 62 is located outside the beam shaping body, while the cylinder body 6 is located inside the proton channel 4 of the beam shaping body BSA and extends into the beam shaping body. One end of the cylinder body 6 outside the beam shaping body 1 is fixedly or movably connected with the target vacuum tube section 62. The target vacuum tube section 62 and the cylinder body 6 can be connected by threads, can be fixedly welded, or can be connected in a flanged manner by disposing a flange on the cylinder body 6 and a flange on the target vacuum tube section 62 (see FIG. 11).

The target body 7 is disposed at an end of the cylinder body 6. The target body 7 and the cylinder body 6 can be slidably adjusted to extend into and out of an interior of the beam shaping body along the proton channel 4 of the beam shaping body BSA.

The current monitoring apparatus 3 includes a monitoring and display device 8 and a connecting conductive wire 9. The monitoring and display device 8 can be a milliammeter, an oscilloscope or a display apparatus on which current data can be directly read, etc.

The contact circuit device 5 includes an adjustable positioning on-off assembly 10 slidably disposed on the cylinder body 6 and a fixed or movable contact conductive assembly 11 disposed outside the beam shaping body 1.

The adjustable positioning on-off assembly 10 includes a sliding positioning part 101, a moving contact part 102 disposed on the sliding positioning part 101, and a conductive circuit 103 connecting the moving contact part 102 and the target body 7. In this embodiment, the moving contact part 102 forms the moving contact 21.

Specifically, the cylinder body 6 is provided with a sliding groove 12. An edge of the sliding groove 12 can be optionally provided with an adjustment scale to facilitate the target assembly 2 to slide into a position of the beam shaping body 1. The scale 0 of the adjustment scale is set on a side of the sliding groove 12 facing an exterior of the beam shaping body 1. This is to facilitate the precise control and adjustment of the position of the target assembly 2 inside the beam shaping body 1, so that the current generated on the target body can be extracted for monitoring under different treatment requirements.

A position of the sliding groove 12 is disposed on the cylinder body 6 at one end close to the target vacuum tube section 62. The sliding groove 12 has a certain axial length, and a specific length of the sliding groove 12 must meet the adjustment range of the cylinder body 6 extending into the interior of the beam shaping body 1, so as to adapt to different treatment requirements and ensure that the current from the accelerator to the cylinder body 6 can be effectively extracted and real-time monitoring can be achieved.

Figure 10:
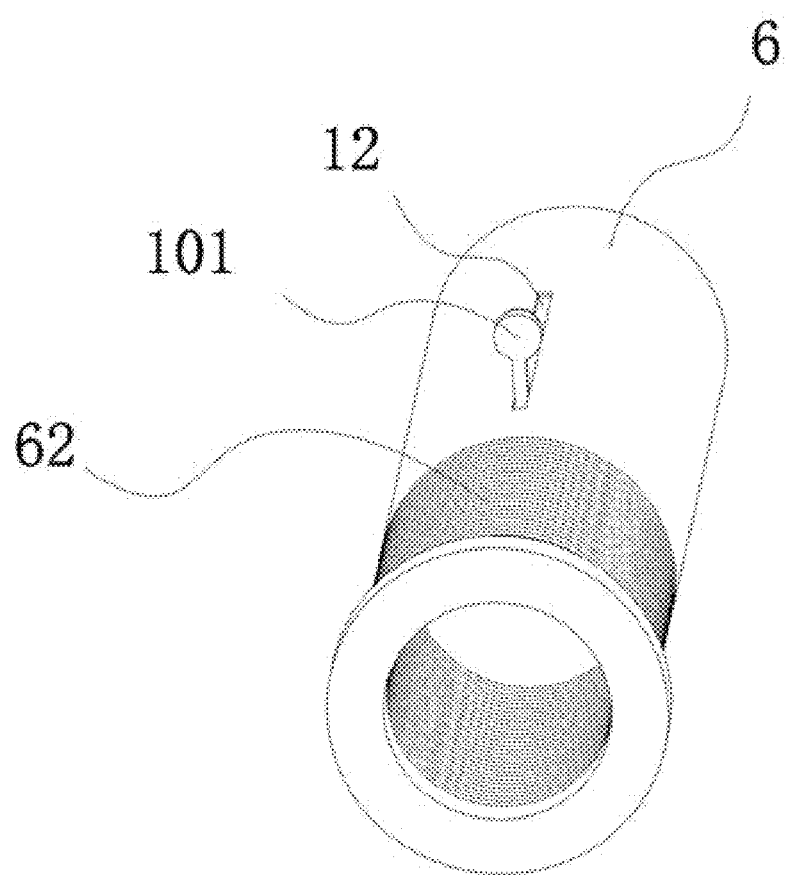
FIG. 10 is a schematic structural diagram of a sliding groove on a cylinder body in the present invention.

As shown in FIG. 10, the sliding groove 12 can be a groove body integrally formed on the cylinder body 6. As shown in FIG. 7, the sliding groove 12 can also be disposed on the cylinder body 6 in an externally added slideway mode. For example, it can be achieved by fixedly connecting a sliding seat 13 with the sliding groove to the cylinder body 6. The sliding groove 12 is insulated from the cylinder body 6.

Figure 11:
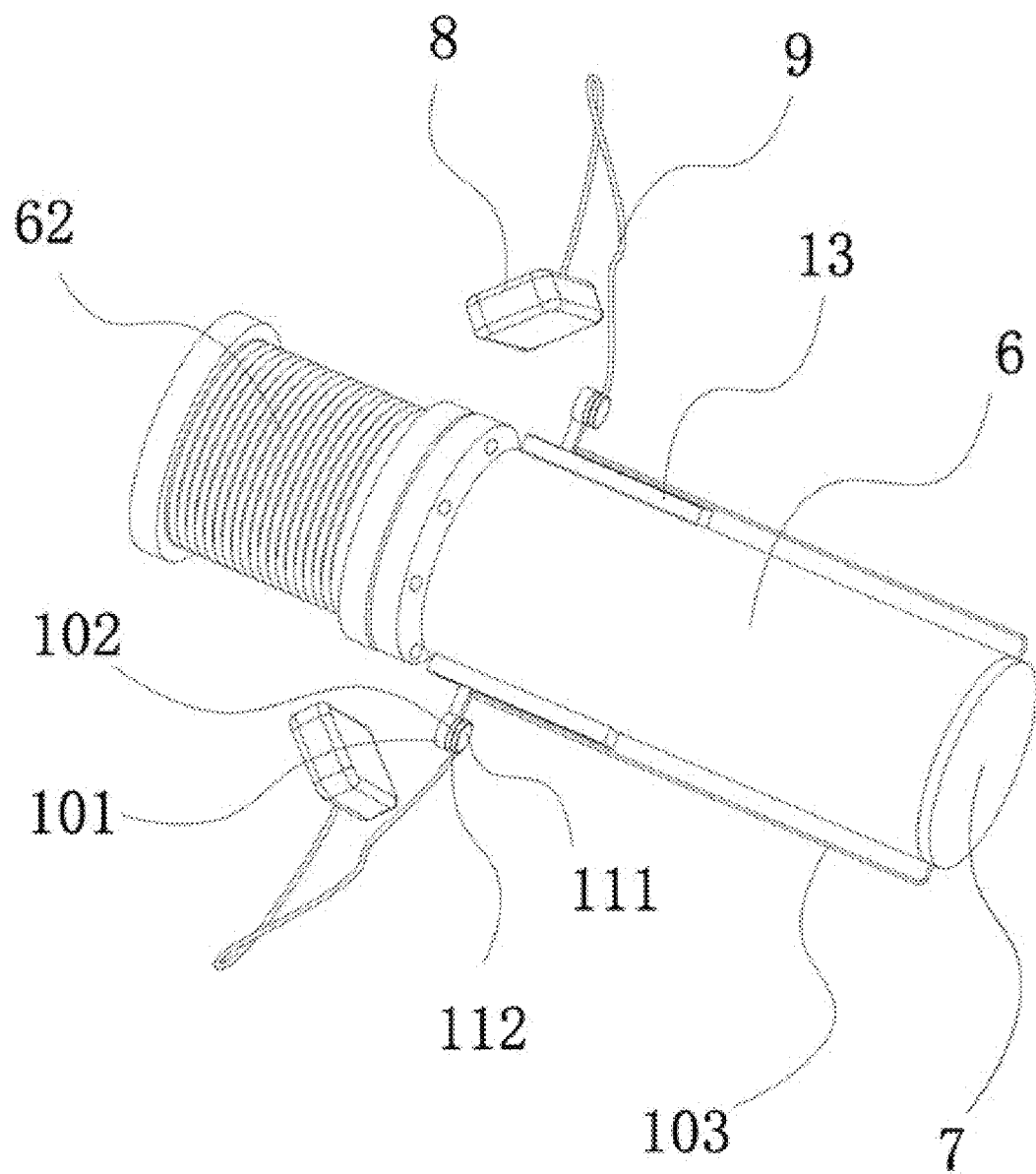
FIG. 11 is a schematic diagram of another connection structure between a contact circuit device and a target assembly in the present invention.

Of course, as shown in FIG. 11, one or a plurality of sliding grooves 12 can be disposed. When the plurality of sliding grooves 12 are disposed, the sliding grooves 12 can be evenly distributed along a circumferential direction of the cylinder body 6, or can be concentrated on one side, or distributed on two sides, or irregularly distributed.

Figure 12:
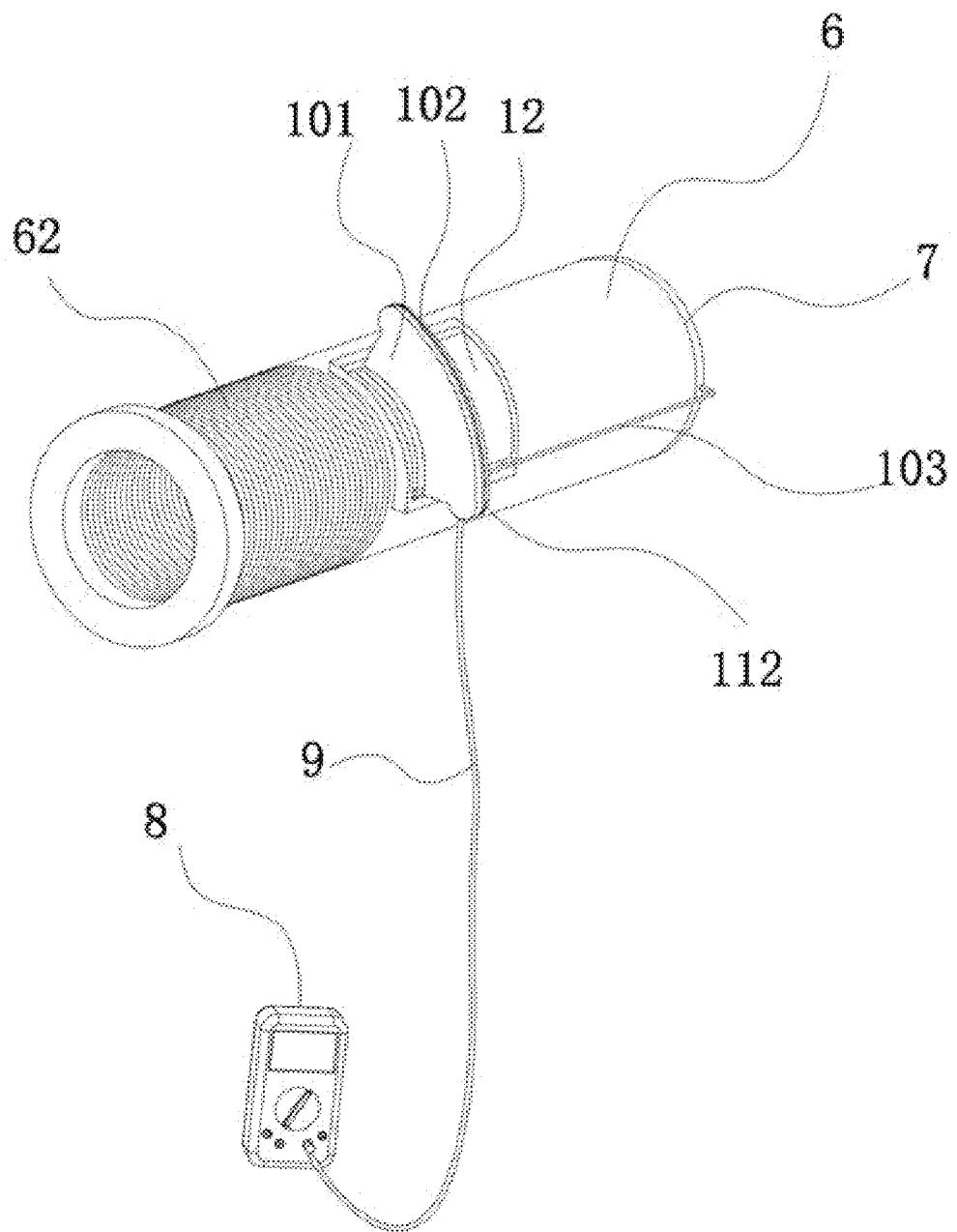
FIG. 12 is a schematic diagram of a third connection structure between a contact circuit device and a target assembly in the present invention.

As shown in FIG. 12, in another embodiment, the sliding groove 12 can be in a fan-shaped structure, that is, the sliding groove 12 is disposed in a fan shape on an outer circumference of the cylinder body 6. At this time, the sliding groove 12 can be directly formed on the cylinder body 6, or can be connected to the cylinder body 6 through a fan shape with the sliding groove 12.

A cross-sectional shape of the sliding groove 12 can be various shapes such as a T shape and a dovetail shape.

The sliding positioning part 101 is slidably disposed inside the sliding groove 12 and is insulated from the sliding groove 12. In this embodiment, the sliding positioning part 101 is a sliding positioning block.

The sliding positioning part 101 is disposed in cooperation according to the number, position and structure of the sliding grooves. The sliding positioning part 101 includes a sliding body 104 adapted to the sliding groove and a contact body 105. The contact body 105 can be in different shapes such as a sheet shape, a ring shape and a point shape. The sliding body 104 can be in different shapes such as a T shape and a dovetail shape. The sliding positioning part 101 is protrudingly disposed on the cylinder body 6 along a radial direction of the cylinder body 6. When the cylinder body 6 moves inside the proton channel 4 of the beam shaping body BSA, the sliding positioning part 101 is always outside the beam shaping body 1.

The moving contact part 102 is disposed in cooperation with the contact body 105. The moving contact part 102 is configured to achieve power on and off. Therefore, the moving contact part 102 can be protrudingly disposed on the contact body 105 or recessedly disposed inside the contact body 105. It can conduct electricity in a male-female contact mode with the contact conductive assembly 11, or can conduct electricity through pressing contact and other different contact conduction modes, that is, any method that can achieve contact for a circuit and non-contact for an open circuit can be adopted.

The conductive circuit 103 connecting the moving contact part 102 and the target body 7 can be directly connected by an electric wire or by a conductive metal wire. The conductive circuit 103 can be of a telescopic type or a fixed type with a certain pulling length.

The contact conductive assembly 11 includes an insulating gasket 111 insulatedly connected with the exterior of the beam shaping body 1 and a stationary contact part 112. In this embodiment, the stationary contact part 112 forms the stationary contact 31. The stationary contact part 112 is disposed in cooperation with the moving contact part 102. The stationary contact part 112 can be one or plural, can be in a sheet shape, a point shape or a ring shape, and can be in a separated structure or an integrated structure.

The stationary contact part 112 and the moving contact part 102 achieve contact for a circuit and conduction and non-contact for an open circuit, that is, the moving contact 21 and the stationary contact 31 achieve contact for a circuit and conduction and non-contact for an open circuit.

The stationary contact part 112 is connected with the monitoring and display device 8 through a connecting conductive wire 9. The stationary contact part 112 can be fixedly connected with the connecting conductive wire or connected in a non-fixed contact mode. As a preferred solution, in this embodiment, the stationary contact part 112 is fixedly connected with the connecting conductive wire by welding. The moving contact part 102 can be in various shapes such as a metal contact, a metal sheet and a metal probe, and the stationary contact part 112 can be in various shapes such as a metal pressing sheet and a metal probe. In this embodiment, the moving contact part 102 can be a metal contact, and the stationary contact part 112 is a metal sheet.

In order to minimize the leakage of radiation, the proton channel 4 of the beam shaping body BSA, on the premise of ensuring that the target assembly 2 can slide and passage of the adjustable positioning on-off assembly 10 is not affected, should adopt as small a sliding gap as possible.

During use, the adjustable positioning on-off assembly 10 moves together with the target assembly 2 along the proton channel 4 of the beam shaping body BSA. At the same time, since the sliding positioning part 101 in the adjustable positioning on-off assembly 10 is protrudingly disposed on the cylinder body 6 along a radial direction of the cylinder body 6, the sliding positioning part 101 is always outside the beam shaping body 1 during movement of the target assembly 2. At the same time, when the cylinder body 6 moves towards the interior of the beam shaping body 1, the sliding positioning part 101 moves outward relative to the sliding groove 12. When the sliding positioning part 101 is in contact with the stationary contact part 112 in the contact conductive assembly 11 outside the beam shaping body 1 to form a circuit (see FIG. 7), a current of the target assembly 2 can be directed into a reading device such as an ammeter in real time.

The core of the technical solution of the boron neutron capture therapy system in the above embodiments is to solve the problem that the hard-wired connection of the target body and the current monitoring apparatus (milliammeter, oscilloscope, etc.) leads to the pulling of the electric wires and the current monitoring apparatus in the target replacement process, and there is a need to manually disconnect the target from the current monitoring apparatus in a radiation environment, which poses a radiation risk. Moreover, since the position of the target in the beam shaping body 1 moves as required, the hard connection between the electric wires and the current monitoring apparatus is not conducive to the movement of the target. Therefore, a contact circuit device 5 is specially disposed on a path of a current circuit, that is, the contact circuit device 5 achieves contact for a circuit and non-contact for an open circuit, so as to avoid the influence on the current monitoring apparatus in the target replacement process.

A sliding positioning part 101 that can move axially and adjust the position is disposed on the cylinder body 6, and the sliding positioning part 101 is insulated from the cylinder body 6. A function of the sliding positioning part 101 is to position the target with an outer side surface of the beam shaping body 1 through mechanical limiting. After the beam conditions are adjusted, a position of the sliding positioning part 101 can be selected, and at this time, the position of the target assembly 2 inside the beam shaping body 1 can be determined.

The sliding positioning part 101 slightly crosses an outer contour edge of the proton channel of the beam shaping body BSA, so that the moving contact part 102 or the moving contact 21 on the sliding positioning part 101 can be in contact with the stationary contact part 112 or the stationary contact 31 disposed at the outer contour edge of the proton channel of the beam shaping body BSA to achieve conduction.

The target body 7 is connected with the moving contact part 102 on the sliding positioning part 101 by an electric wire or a conductive wire. A contact conductive assembly 11 is disposed at the outer contour edge of the proton channel 4 of the beam shaping body BSA, and the contact conductive assembly 11 is insulated from the beam shaping body.

When the target reaches the designated position, the moving contact part 102 of the sliding positioning part 101 is connected with the externally disposed stationary contact part 112 for conduction. The stationary contact part 112 is externally connected to an ammeter through an electric wire, and finally the current of the target is directed into the ammeter.

When a new target assembly extends into the BSA, in order to adjust the position of the target assembly 2 inside the beam shaping body 1, only the position of the sliding positioning part 101 needs to be adjusted. While this is also applicable to defining the position of the target assembly 2, the moving contact part 102 on the sliding positioning part 101 is connected with the stationary contact part 112 for conduction. In this way, it is possible to avoid the influence on the apparatus when the target assembly 2 is replaced, or the radiation risk caused by the need for manual disconnection of the circuit.

Since the position of the target assembly 2 inside the beam shaping body 1 is adjusted according to the treatment requirements, in order to ensure that the current from the accelerator to the target assembly 2 can be extracted through the ammeter under any treatment requirements, the sliding positioning part 101 has certain sliding space on the cylinder body 6 to meet the needs of the target assembly extending into different positions of the beam shaping body. In this way, when the target assembly 2 is replaced, an electric wire or a conductive wire between the cylinder body 6 and the sliding positioning part 101 is short and is integrally disposed with the cylinder body 6, and can be stored in a waste target box together. A current reading device is only connected with the stationary contact part 112 on an outer side of the beam shaping body, which will not involve the reading device and will not bring a new burden to the storage of the target assembly.

The sliding positioning part 101 also needs to be made insulating, that is, when the target assembly is connected with the moving contact part 102 on the sliding positioning part 101 through an electric wire, it is still insulated from other components such as the sliding positioning part 101.

The target body 7 needs to be insulated from a front end, and at the same time, the target body is not in contact with the beam shaping body, that is, the target body is insulated everywhere.

The specific operation mode of the boron neutron capture therapy system is as follows.

First, the sliding positioning part 101 on the target assembly is adjusted. According to the position where the target assembly is to extend into the beam shaping body, the position of the sliding positioning part 101 on the cylinder body 6 is adjusted. When the target assembly extends into the beam shaping body to the set position and is positioned, the moving contact part 102 or the moving contact 21 on the sliding positioning part 101 is in contact with the stationary contact part 112 or the stationary contact 31, and a conductive circuit is formed between the monitoring apparatus and the target assembly to achieve conduction.

Second, the stationary contact part 112 is connected with an external ammeter through an electric wire. When the target is in contact with the pressing sheet or the probe, the target body, the moving contact part 102 or the moving contact 21 on the sliding positioning part 101, the stationary contact part 112 or the stationary contact 31, and the ammeter form a circuit.

Third, when the target assembly is replaced, the target assembly is drawn out from the interior of the beam shaping body by a robotic arm. The moving contact part 102 or the moving contact 21 on the sliding positioning part 101 on the body 6 is disengaged from the stationary contact part 112 or the stationary contact 31, and an open circuit is formed between the target assembly and the ammeter. At this time, the target assembly can be normally and automatically replaced and stored.

The boron neutron capture therapy system achieves the current measurement of the target on the premise of fully automatic target replacement. This solves the problem of increased operating costs caused by the need to manually remove the electric wire connecting the ammeter and the target at the radiation site or to store the target and the ammeter together.

Through the moving contact part 102 on the sliding positioning part 101 and the stationary contact part 112 on the outer side of the beam shaping body, contact current monitoring is achieved, and it does not affect the storage of the target when the target is replaced. Moreover, the electric wire can be extended, and the ammeter is placed in a non-radiation area, which improves the service life of the apparatus.

Through the current measurement method of this solution, it is possible to avoid a certain amount of the influence of the current extraction device on the beam inside the proton channel. All components are arranged on the outer side of the beam shaping body.

The sliding positioning part 101, the moving contact part 102 and the stationary contact part 112 in the boron neutron capture therapy system can adopt metal contacts and metal sheets or other conductive materials, and the shape can be any other shape and is not limited to the shape in the schematic diagrams. The purpose is still to extract the current of the target body.

The metal contact can be made into other shapes, such as a metal spring contact, etc., which can achieve conduction and at the same time avoid the hard-wired contact between the target positioning block and the outer side of the beam shaping body and increase the contact area. The metal sheet can also be made into various shapes to increase the contact probability between the metal contact and the metal sheet.

The above specific implementations/embodiments are the descriptions of the embodiments specific to the present invention, which are used to illustrate the concept of the present invention. They are all explanatory and exemplary, and should not be construed as limitations on the implementations of the present invention and the scope of the present invention. In addition to the embodiments described herein, those skilled in the art can also adopt other obvious technical solutions based on the contents disclosed in the claims and the specification of this application. These technical solutions include technical solutions that make any obvious substitutions and modifications to the embodiments described herein, and are all within the scope of protection of the present invention.

What is claimed is:

1. A boron neutron capture therapy system, comprising a beam shaping body with a proton channel and a target assembly disposed inside the proton channel, wherein the target assembly is replaceable, a current monitoring apparatus is disposed outside the beam shaping body, the target assembly is provided with a moving contact, and the current monitoring apparatus is provided with a stationary contact forming a moving contact conductive mode with the moving contact.

2. The boron neutron capture therapy system according to claim 1, wherein the moving contact and the stationary contact are disposed on a contact circuit device implementing the moving contact conductive mode.

3. The boron neutron capture therapy system according to claim 1, wherein the current monitoring apparatus comprises an external monitoring and display device.

4. The boron neutron capture therapy system according to claim 1, wherein a scale for implementing a position adjustment is disposed on the target assembly.

5. The boron neutron capture therapy system according to claim 2, wherein the contact circuit device comprises an adjustable positioning on-off assembly slidably disposed on the target assembly and a contact conductive assembly disposed outside the beam shaping body.

6. The boron neutron capture therapy system according to claim 2, wherein the target assembly comprises a cylinder body and a target body, the target body is disposed at an end of the cylinder body extending into an interior of the beam shaping body, and the target body, the contact circuit device, and the current monitoring apparatus form a circuit.

7. The boron neutron capture therapy system according to claim 5, wherein the moving contact is disposed on the adjustable positioning on-off assembly, and the stationary contact is disposed on the contact conductive assembly, and when the adjustable positioning on-off assembly is in contact with the contact conductive assembly for conduction, a current monitoring circuit is formed among the target assembly, the adjustable positioning on-off assembly, the contact conductive assembly, and the current monitoring apparatus.

8. The boron neutron capture therapy system according to claim 7, wherein the target assembly comprises a cylinder body and a target body, the target body is disposed at an end of the cylinder body extending into an interior of the beam shaping body, and the target body, the contact circuit device, and the current monitoring apparatus form a circuit.

9. The boron neutron capture therapy system according to claim 5, wherein the adjustable positioning on-off assembly comprises an insulating sliding positioning part, a moving contact part is fixedly connected with the insulating sliding positioning part, and the moving contact part is electrically connected to the target assembly through a conductive circuit.

10. The boron neutron capture therapy system according to claim 9, wherein the moving contact is disposed on the moving contact part, or the moving contact part forms the moving contact.

11. The boron neutron capture therapy system according to claim 10, wherein the target assembly comprises a cylinder body and a target body, the target body is disposed at an end of the cylinder body extending into an interior of the beam shaping body, and the target body, the contact circuit device, and the current monitoring apparatus form a circuit.

12. The boron neutron capture therapy system according to claim 9, wherein the target assembly is provided with a sliding groove, and the insulating sliding positioning part is slidably disposed inside the sliding groove and is located outside the beam shaping body.

13. The boron neutron capture therapy system according to claim 12, wherein the target assembly comprises a cylinder body and a target body, the target body is disposed at an end of the cylinder body extending into an interior of the beam shaping body, and the target body, the contact circuit device, and the current monitoring apparatus form a circuit.

14. The boron neutron capture therapy system according to claim 9, wherein the target assembly comprises a cylinder body and a target body, the target body is disposed at an end of the cylinder body extending into an interior of the beam shaping body, and the target body, the contact circuit device, and the current monitoring apparatus form a circuit.

15. The boron neutron capture therapy system according to claim 5, wherein the contact conductive assembly comprises a stationary contact part disposed outside the beam shaping body and located at an outer edge of the proton channel, and the stationary contact part is electrically connected to the current monitoring apparatus.

16. The boron neutron capture therapy system according to claim 15, wherein the stationary contact is disposed on the stationary contact part, or the stationary contact part forms the stationary contact.

17. The boron neutron capture therapy system according to claim 16, wherein the target assembly comprises a cylinder body and a target body, the target body is disposed at an end of the cylinder body extending into an interior of the beam shaping body, and the target body, the contact circuit device, and the current monitoring apparatus form a circuit.

18. The boron neutron capture therapy system according to claim 15, wherein the stationary contact part is fixed outside the beam shaping body, or the stationary contact part is movably disposed on the beam shaping body.

19. The boron neutron capture therapy system according to claim 15, wherein the target assembly comprises a cylinder body and a target body, the target body is disposed at an end of the cylinder body extending into an interior of the beam shaping body, and the target body, the contact circuit device, and the current monitoring apparatus form a circuit.

20. The boron neutron capture therapy system according to claim 5, wherein the target assembly comprises a cylinder body and a target body, the target body is disposed at an end of the cylinder body extending into an interior of the beam shaping body, and the target body, the contact circuit device, and the current monitoring apparatus form a circuit.

\* \* \* \* \*